United States Patent [19]
Yuen et al.

[11] Patent Number: 5,766,582
[45] Date of Patent: Jun. 16, 1998

[54] STABLE, AQUEOUS ALFA INTERFERON SOLUTION FORMULATIONS

[75] Inventors: Pui-Ho C. Yuen, Princeton Junction; Douglas F. Kline, Hoboken, both of N.J.

[73] Assignee: Schering Corporation, Kenilworth, N.J.

[21] Appl. No.: 329,813

[22] Filed: Oct. 11, 1994

[51] Int. Cl.$^6$ .................................................. A61K 38/21
[52] U.S. Cl. ................................................................. 424/85.7
[58] Field of Search ............................................... 424/85.7

[56] References Cited

U.S. PATENT DOCUMENTS

| | | | |
|---|---|---|---|
| 4,496,537 | 1/1985 | Kwan | 424/85 |
| 4,606,917 | 8/1986 | Eppstein | 424/85 |
| 4,675,183 | 6/1987 | Kato et al. | 424/85 |
| 4,680,175 | 7/1987 | Estis et al. | 424/85 |
| 4,847,079 | 7/1989 | Kwan | 424/85.7 |
| 4,857,316 | 8/1989 | Eppstein | 424/85.6 |
| 5,266,310 | 11/1993 | Mundorf et al. | 424/85.1 |
| 5,503,827 | 4/1996 | Woog et al. | 424/85.1 |

FOREIGN PATENT DOCUMENTS 0284249  9/1988  European Pat. Off. .

OTHER PUBLICATIONS

Derwent Abstract, Database WPI, Derwent AN 87–018978; Class B04; Derwent Publications, Ltd. London, GB; Abstract of Japanese published patent appln. JP. A. 61277633 (Toray Industries, Inc.); published Dec. 8, 1986.

Derwent Abstract, Database WPI, Derwent AN 84–285358; Class B04; Derwent Publications Ltd., London, G.B.; Abstract of Japanese Published Patent Appln. JPA 59176216 (Sumitomo Chemical KK); published Oct. 5, 1984.

*Primary Examiner*—Chhaya D. Sayala
*Attorney, Agent, or Firm*—Thomas D. Hoffman

[57] ABSTRACT

Process for making stable aqueous solution formulations containing alfa-type interferon, e.g., interferon alfa-2a and interferon alfa-2b, a buffer to maintain the pH in the range of 4.5–7.1, polysorbate 80 as a stabilizer, edetate disodium as a chelating agent, sodium chloride as a tonicity agent, and m-cresol as an antimicrobial preservative and which maintain high chemical, physical and biological stability of the alfa interferon for an extended storage period of at least 24 months are disclosed.

11 Claims, No Drawings

STABLE, AQUEOUS ALFA INTERFERON SOLUTION FORMULATIONS

BACKGROUND OF THE INVENTION

This invention relates to stable, aqueous solution formulations which are free of products derived from human blood serum and which maintain high biological activity and high chemical and high physical stability of alfa-type interferon for an extended period of time.

U.S. Pat. No. 4,496,537 discloses biologically stable alfa interferon aqueous solution formulations containing alfa interferon, human serum albumin and alanine or glycine, water, and a buffer system to maintain the pH at 6.5–8.0. The human serum albumin ("HSA") acts as a stabilizer for alfa interferon and prevents losses of alfa interferon from solution by coating and/or adsorption of the alfa interferon onto the stainless steel and glass surfaces of compounding vessels, process equipment and storage containers. Solution formulations containing alfa interferon and HSA have maintained the chemical and biological stability of the alfa interferon when such solutions have been stored at 2°–8° C. for extended periods, i.e., more than 2 years.

Recently, the worldwide AIDS epidemic has resulted in health registration agencies requiring manufacturers to place warnings on products, such as alfa interferon, which contain products derived from human blood such as HSA.

There is a need to reformulate alfa-interferon solution products to obtain a solution formulation free of human blood-derived products such as HSA while maintaining high chemical, high physical stability and high biological activity for alfa interferon in the aqueous solution formulations for extended storage periods.

SUMMARY OF THE INVENTION

The present invention provides a stable, aqueous solution formulation which maintains high biological activity for alfa-interferon and is free of human blood-derived products which comprises:

a. $0.1 \times 10^6$ to $100 \times 10^6$ IU/mL of alfa interferon;
b. a buffer system to maintain a pH in the range of 4.5 to 7.1.
c. an effective amount of a chelating agent;
d. an amount of a sorbitan mono-9-octadecenoate poly (oxy-1,2-ethanediyl) derivative sufficient to stabilize the alfa-interferon against loss of alfa-type interferon;
e. an effective amount of a tonicity agent;
f. an effective amount of an antimicrobial preservative; and
g. an amount of water for injection sufficient to prepare a solution of the above-listed ingredients.

The present invention provides a stable, aqueous solution formulation having high alfa interferon biological activity and free of human blood-derived products which comprises:

a. $0.1 \times 10^6$ to $100 \times 10^6$ IU/mL of alfa interferon.
b. a buffer system sufficient to maintain the pH of the solution in the range of 4.5 to 7.1;
c. about 0.01 to 1 mg/mL of disodium dihydrogen ethylenediaminetetraacetate.
d. about 0.01 to 1 mg/mL of a sorbitan mono-9-octadecenoate poly(oxy-1,2-ethanediyl) derivative;
e. about 1 to 9 mg/mL of sodium chloride;
f. an effective amount of an antimicrobial preservative selected from m-cresol, phenol, methylparaben, propylparaben or mixtures thereof; and
g. water for injection q.s. ad. 1 mL.

In a preferred aspect, the present invention provides a stable, aqueous solution formulation having high biological alfa interferon activity and free of human blood-derived products, which comprises:

|  | mg/mL |
|---|---|
| a. Alfa-2 Interferon | $5 \times 10^6$ to $50 \times 10^6$ IU |
| b. Sodium Phosphate Dibasic Anhydrous | 1.8 |
| c. Sodium Phosphate Monobasic Monohydrate | 1.3 |
| d. Disodium Dihydrogen Ethylenediaminetetraacetate | 0.1 |
| e. Polysorbate 80 | 0.1 |
| f. Methylparaben | 1.2 |
| g. Propylparaben | 0.12 |
| h. Sodium Chloride; and | 7.5 |
| i. Water for Injection | q.s. ad 1 mL |

In another preferred aspect the present invention further provides a stabile aqueous solution formulation having high biological alfa interferon activity and free of human blood-derived products, which comprises:

|  | mg/mL |
|---|---|
| a. Alfa-2 Interferon | $5 \times 10^6$ to $50 \times 10^6$ IU |
| b. Sodium Phosphate Dibasic Anhydrous | 1.8 |
| c. Sodium Phosphate Monobasic Monohydrate | 1.3 |
| d. Disodium Dihydrogen Ethylenediaminetetraacetate | 0.1 |
| e. Polysorbate 80 | 0.1 |
| f. m-Cresol | 1.5 |
| g. Sodium Chloride; and | 7.5 |
| h. Water for Injection | q.s. ad 1 mL |

The present invention also provides a process of preparing a stable, aqueous solution formulation having high biological alfa interferon activity and free of human blood-derived products comprising admixing an effective amount of alfa interferon with a buffer system capable of maintaining the pH within the range of 4.5 to 7.1, a chelating agent, a sorbitan mono-9-octadecenoate poly(oxy-1,2-ethanediyl) derivative, a tonicity agent, an antimicrobial preservative and water to form a solution. In a preferred aspect of the process of the present invention, the solution is prepared and maintained substantially free of dissolved oxygen and a headspace of inert atmosphere above the solution is maintained at a value of less than about 4% by volume of oxygen.

DETAILED DESCRIPTION

We have selected specific amounts of a specific set of ingredients that have allowed us to develop an aqueous alfa interferon solution formulation which does not contain human serum albumin yet maintains high chemical, biological and physical stability for the alfa interferon on storage at 2° to 8° C. for extended periods of at least 24 months.

The term "free of human blood-derived products" as used herein in reference to the formulations of the present invention means that no human blood-derived products such as HSA are used in the preparation of the solution formulations of the present invention.

The term "high chemical stability" as used herein in reference to the alfa interferon used in the formulations of the present invention means the alfa interferon maintains at least 85%, preferably 85% to 100% of its chemical integrity upon storage at 2° to 8° C. for at least 24 months. See Tables 1 and 2. The chemical integrity is determined by measuring the protein content in an HPLC assay such as the one disclosed by T. L. Nagabhushan, et al., in an article entitled "Characterization of Genetically Engineered ALFA-2 Interferon", pages 79–88 appearing in *Interferon Research Clinical Application, and Regulatory Consideration*, Zoon, et al., eds., Elsevier Science Publishing Co., Inc. 1984. (See results in Tables 1 to 4).

The term "high biological stability" as used herein in reference to the alfa interferon used in the formulations of the present invention means the alfa type interferon in the formulation maintains at least 75%, preferably at least 85%, more preferably 90% to 100% of its biological activity upon storage at 2° to 8° C. for at least 24 months (see results in Tables 1 to 4) as measured in the standard method of inhibition of the cytopathic effect (CPE) of a virus such as the method disclosed by W. P. Protzman, et al., in *J. Clinical Microbiology*, (1985), 22, 596–599.

The term "high physical stability" as used herein in reference to the alfa interferon used in the formulations of the present invention means the formulation of the present invention remains clear, i.e., does not exhibit haze or visible particulate matter (i.e., particles greater than about 60 to 70 microns in diameter) on storage at 2° to 8° C. for at least 24 months. See Tables 1, 2 and 3. The results listed in Tables 1, 2 and 3 are surprising in that most solution formulations containing protein products like alfa interferon tend to develop visually observable particulate matter (i.e., particles having diameters greater than 60 to 70 microns) upon extended storage even at 2° to 8° C. The test method used to determine particulate matter in the solution formulation of this invention (see Tables 1 to 4) is described in The United States Pharmacopeia/The National Formulary USP XXII/NF XVII, published by United States Pharmacopeial Convention, Inc., (1990), Rockville, Md.; see Physical Test <788> on pages 1596 to 1598. The method used to determine the visual description of the solution formulations of this invention is also described in USP XXII as the "General Requirement Test and Assays <1> Injections" at pages 1470 to 1472.

We have found that by adding a chelating agent to the formulations of the present invention, we have been able to avoid visible particulate matter. Typical suitable chelating agents include disodium dihydrogen ethylenediamine tetraacetate (EDTA or edetate disodium) or citric acid. The use of edetate disodium is preferred. While we do not wish to be bound by any theory, it is believed that edetate disodium effectively complexes with trace amounts of metal cations, such as $Zn^{2+}$, $Fe^{2+}$, $Cu^{2+}$ or $Al^{3+}$, which ions may be present in excipients and packaging components, e.g., rubber stoppers or gaskets. Since edetate disodium has a higher affinity for these metal cations than the alfa interferons, the interaction between metal cations and alfa interferon which results in formation of insoluble complexes (in the form of, for example, visible particulate matter) and loss of activity are avoided. The effective amount of the chelating agent is in the range of 0.01 to 1 mg/mL based on $0.1 \times 10^6$ to $100 \times 10^6$ International Units ("IU") of alfa type interferon/mL. Preferably, 0.1 mg of edetate disodium is used for $5 \times 10^6$ to $50 \times 10^6$ IU of alfa-2 interferon.

The buffer systems suitable for the formulations of the present invention are those which maintain the pH of the aqueous solution formulation in the range of 4.5 to 7.1, preferably 6.5–7.1 and most preferably 6.8. The use of a buffer system of sodium phosphate dibasic and sodium phosphate monobasic is preferred. Normally a 0.005 to 0.1 molar buffer of the preferred sodium phosphate monobasic/dibasic buffer system is used for a formulation containing $0.1 \times 10^6$ to $100 \times 10^6$ IU of alfa interferon per mL. Other suitable buffer systems to maintain the desired pH range of 4.5 to 7.1 include sodium citrate/citric acid and sodium acetate/acetic acid.

The tonicity agent useful in the present invention is any agent capable of rendering the formulations of the present invention iso-osmotic with human serum. Typical suitable tonicity agents include sodium chloride, mannitol, glycine, glucose and sorbitol. Use of sodium chloride as a tonicity agent is preferred.

The amount of the tonicity agent used is in the range of 1 to 10 mg/mL when the formulation of the present invention contains $0.1 \times 10^6$ to $100 \times 10^6$ IU of alfa interferon/mL. The use of 7.5 mg/mL of sodium chloride is preferred for $5 \times 10^6$ to $50 \times 10^6$ IU of alfa interferon per mL in the formulations of the present invention.

The sorbitan mono-9-octadecenoate poly(oxy-1,2-ethanediyl) derivatives such as polysorbate 80 or polysorbate 20 are useful as a stabilizing agent to prevent adsorption of the alfa interferon proteins such as alfa-2b interferon onto the stainless steel and glass surfaces of the equipment used to make the indictable formulations containing alfa interferon. The amount of polysorbate 20 or 80 effective in the formulation of this invention is in the range of 0.01 to 1.0 mg 3 0 per mL for a formulation containing $0.1 \times 10^6$ to $100 \times 10^6$ IU of alfa interferon per mL. The use of polysorbate 80 is preferred. The use of 0.1 mg/mL of polysorbate 80 is more preferred in all the solution formulations of the present invention. When the concentrations of alfa interferon such as alfa-2 interferon is less than about $15 \times 10^6$ IU/mL, e.g., $6 \times 10^6$ IU/mL, loss of activity due to adsorption of the alfa interferon in the absence of polysorbate 80 significantly lowers the biological activity of the formulation. Surprisingly, we have found that polysorbate 80 prevents loss of alfa-2b interferon and allows systemic delivery of the alfa-2b interferon without loss of biological activity. In the course of development of the formulation of the present invention, we surprisingly found that polysorbate 80 provided superior chemical and biological stability to alfa-2b interferon compared to other non-ionic surfactants, e.g., Pluronic F127 and Pluronic F-68.

The amount of alfa interferon useful in the formulation of the present invention is in the range of $0.1 \times 10^6$ to $100 \times 10^6$ IU/mL, preferably $5 \times 10^6$ to $50 \times 10^6$ IU/mL.

The term "alfa interferon" as used herein means the family of highly homologous species-specific proteins that inhibit viral replication and cellular proliferation and modulate immune response. Typical suitable alfa interferons include interferon alfa-2a such as ROFERON A interferon alfa-2a available from Hoffmann-La Roche, Nutley, N.J., interferon alfa-2b such as INTRON A interferon alfa-2b available from Schering Corporation, Kenilworth, N.J. interferon alfa-2c such as BEROFOR interferon alfa-2c available from Boehringer Ingelheim Pharmaceutical, Inc., Ridgefield, Conn., interferon alfa-n1, a purified blend of natural alfa interferons such as SUMIFERON available from Sumitomo, Japan or as WELLFERON interferon alfa-n1 available from The Wellcome Foundation Ltd., London, Great Britain, or consensus alfa interferon available from Amgen, Inc., Newbury Park, Calif., or interferon alfa-n3, a mixture of natural alfa interferons, made by Interferon Sciences and available from the Purdue Frederick Co., Norwalk, Conn., under the ALFERON tradename. The use of interferon alfa-2a or alfa-2b is preferred. The use of interferon alfa-2b is more preferred.

The antimicrobial preservatives found useful in the present invention include m-cresol, phenol and methylparaben and propylparaben and mixtures of the above-listed preservatives, e.g., phenol-methylparaben mixtures. The effective amount of m-cresol found useful in the present invention is in the range of 0.5 to 2 mg/mL for a formulation containing $0.1 \times 10^6$ to $100 \times 10^6$ IU/mL of alfa interferon. It is preferred to use 1.5 mg/mL of m-cresol for a formulation containing $5 \times 10^6$ to $50 \times 10^6$ IU/mL of interferon alfa-2b.

The effective amount of phenol found useful is in the range of 0.5 to 5 mg/mL for a solution formulation containing $0.1 \times 10^6$ to $100 \times 10^6$ IU/mL of alfa interferon.

The effective amount of methylparaben is in the range of 0.6 to 1.8 mg/mL and the amount of propylparaben is in the range of 0.06 to 0.18 mg/mL when the formulation of the present invention contains $0.1 \times 10^6$ to $100 \times 10^6$ IU/mL of alfa interferon.

It is preferred to use 1.2 mg/mL of methylparaben in combination with 0.12 mg/mL of propylparaben when the formulation of the present invention contains $0.1 \times 10^6$ to $100 \times 10^6$ IU/mL of alfa-2b interferon.

The use of m-cresol as an antimicrobial preservative is more preferred.

The water used for preparation of the formulations of the present invention is preferably water for injection.

During the course of development of the aqueous solution formulations of the present invention that would maintain high biological activity as well as high chemical and high physical stability of the alfa interferon over an extended storage period without employing HSA as a stabilizer, we identified that the amount of a sorbitan mono-9-octadecenoate poly(oxy-1,2-ethanediyl) derivative such as polysorbate 80 required to act as a stabilizing agent for the alfa interferon had a direct effect on the effective amount of the antimicrobial preservative which could be added to the aqueous solution formulation to provide the appropriate antimicrobial protection for said formulation pursuant to various worldwide health registration requirements without causing undesirable haze formation in the solution.

Thus, when the preferred stabilizing agent, polysorbate 80,was present in formulations of the present invention, in the preferred effective amount of 0.1 mg/mL, the effective amount of the preferred antimicrobial preservative, e.g., m-cresol which could be added without causing hazing of said formulation was found to be critical. For example if the amount of m-cresol added to a formulation which contained 0.1 mg/mL of polysorbate 80,such as shown in Example 3,is increased to greater than 1.75 mg/mL, hazing was observed. A similar hazing problem was observed when the amount of polysorbate 80 in the resultant formulation was varied from 0.01 to 1 mg/mL. No hazing was observed when 1.75 mg/mL or less, preferably about 1.5 mg/mL of m-cresol was added to a formulation prepared in accordance with the procedures of Example 3 which contains 0.1 mg/mL of polysorbate 80. This criticality was also observed with the parabens and phenol when they were used as antimicrobial preservatives. For formulations of the present invention containing 0.01 to 1 mg/mL of polysorbate 80,the effective amount of methylparaben should be no more than about 1.2 mg/mL when used with 0.12 mg/mL of propylparaben to avoid hazing, and the effective amount of phenol (when it is used in place of the parabens) should be in the range of 0.5 to less than about 4 mg/mL to avoid hazing.

Alfa-type interferon formulations are useful for treatment of a variety of disease states such as renal cell carcinomas, AIDS-related Kaposi's sarcoma, chronic and acute hepatitis B, chronic and acute non-A, non-B/C hepatitis. The formulations of the present invention are useful in treating these disease states preferably as injectable aqueous solutions.

EXAMPLES

The following non-limiting examples illustrate the preparation of the aqueous solutions of alfa type interferons.

The procedures listed after Example 5 are used to prepare the formulations of the present invention of Examples 1 to 5.

Example 1

| | | |
|---|---|---|
| Active Substance: | Interferon alfa-2b | $0.1 \times 10^6 - 100 \times 10^6$ IU/mL* |
| Buffer: | Sodium Phosphate (monobasic/dibasic) | 0.005–0.1 M |
| Chelating Agent: | Edetate Disodium | 0.01–1 mg/mL |
| Stabilizer: | Polysorbate 80 | 0.01–1 mg/mL |
| Tonicity Adjusting Agent: | Sodium Chloride | 1–9 mg/mL |
| Antimicrobial Preservative: | m-Cresol | 0.5–1.75 mg/mL |
| | or Phenol | 0.5–<4 mg/mL |
| | or Methylparaben | 0.6–1.2 mg/mL |
| | Propylparaben | 0.06–0.12 mg/mL |
| Solvent: | Water for Injection q.s. ad | 1 mL |

*IU-International Units

Example 2

| | |
|---|---|
| Interferon alfa-2b | $10 \times 10^6$ IU/mL |
| Sodium Phosphate Dibasic Anhydrous | 1.8 mg/mL |
| Sodium Phosphate Monobasic Monohydrate | 1.3 mg/mL |
| Edetate Disodium | 0.1 mg/mL |
| Polysorbate 80 | 0.1 mg/mL |
| Methylparaben | 1.2 mg/mL |
| Propylparaben | 0.12 mg/mL |
| Sodium Chloride | 7.5 mg/mL |
| Water for injection q.s. ad | 1 mL |

Example 3

| | |
|---|---|
| Interferon alfa-2b | $10 \times 10^6$ IU/mL |
| Sodium Phosphate Dibasic Anhydrous | 1.8 mg/mL |
| Sodium Phosphate Monobasic Monohydrate | 1.3 mg/mL |
| Edetate Disodium | 0.1 mg/mL |
| Polysorbate 80 | 0.1 mg/mL |
| m-Cresol | 1.5 mg/mL |
| Sodium Chloride | 7.5 mg/mL |
| Water for Injection q.s. ad | 1 mL |

Stability data on Examples 2 and 3 are summarized in Tables 1 and 2 respectively.

Example 4

The formulation of Example 3 was prepared with $6 \times 10^6$ IU/mL of alfa-2b interferon in accordance with the method of manufacture detailed herein below using nitrogen sparging of the solution and maintaining no more than about 4% by volume of oxygen in the headspace.

Vials containing a label volume of 3 mL of solution were stored at 30°, 25° and 4° C. The results are summarized in Table 3

Example 5

The formulation of Example 4 was prepared in accordance with the method of manufacture detailed hereinbelow in all details except no nitrogen was sparged through the solution or overlaid upon it and the oxygen volume in the headspace was ~20% by volume as found in ambient air.

Vials containing a label volume of 3 mL of solution were stored at 30°, 25° and 4° C. The results are summarized in Table 4.

Similar results are expected if the interferon alfa-2b in Examples 1 to 5 is substituted by an equivalent amount of Roferon A, Wellferon or Sumiferon interferon alfa.

TABLE 1

Interferon Alfa-2b Stability Data on Example 2

| Time (month) | Temp (°C.) | Anti-Viral Assay (CPE) | | Protein Content (HPLC Assay) | | Particulate Matter (particles/container) | | | Description |
|---|---|---|---|---|---|---|---|---|---|
| | | ($\times 10^6$ IU/mL) | (% L.S.) | (mcg/mL) | (% of Initial) | $\geq 10\mu$ | $\geq 25\mu$ | $\geq 50\mu$ | |
| Initial | | 10.0 | 100 | 42.5 | 100 | 40 | 3 | 1 | ccs* |
| 3 | 4 | 9.0 | 90 | 42.4 | 100 | 16 | 13 | 11 | ccs |
| 6 | 4 | 10.0 | 100 | 41.8 | 98 | 8 | 3 | 1 | ccs |
| 9 | 4 | 10.0 | 100 | 43.3 | 102 | 52 | 3 | 0 | ccs |
| 12 | 4 | 10.0 | 100 | 44.3 | 104 | 17 | 4 | 2 | ccs |
| 18 | 4 | 9.8 | 98 | 41.5 | 98 | 6 | 1 | 0 | ccs |
| 24 | 4 | 10.0 | 100 | 39.5 | 93 | 5 | 1 | 0 | ccs |

*ccs - clear, colorless solution, essentially free of visible particles.

TABLE 2

Interferon Alfa 2b Stability Data on Example 3

| Time (month) | Temp (°C.) | Anti-Viral Assay (CPE) | | Protein Content (HPLC Assay) | | Particulate Matter (particles/container) | | | Description |
|---|---|---|---|---|---|---|---|---|---|
| | | ($\times 10^6$ IU/mL) | (% L.S.) | (mcg/mL) | (% of Initial) | $\geq 10\mu$ | $\geq 25\mu$ | $\geq 50\mu$ | |
| Initial | | 10.3 | 103 | 40.3 | 100 | 68 | 4 | 3 | ccs* |
| 1 | 4 | 10 | 100 | 40.6 | 101 | 142 | 24 | 23 | ccs |
| 3 | 4 | 10 | 100 | 41.4 | 103 | 311 | 63 | 35 | ccs |
| 6 | 4 | 10 | 100 | 42.5 | 105 | 206 | 17 | 16 | ccs |

*ccs - clear, colorless solution, essentially free of visible particles.

TABLE 3

Interferon Alfa 2b Stability Data on Example 4

| Time (month) | Temp (°C.) | Position of Vial* | Anti-Viral Assay (CPE) | | Protein Content (HPLC Assay) | | m-Cresol Assay | | |
|---|---|---|---|---|---|---|---|---|---|
| | | | ($\times 10^6$ IU/mL) | (% L.S.) | (mcg/mL) | (% of Initial) | (mg/mL) | % LS | pH |
| Initial | | | 6.48 | 108 | 25.7 | 100 | 1.47 | 98.0 | 6.91 |
| 1 | 30 | UP | 6.00 | 100 | 24.8 | 96.5 | 1.47 | 98.0 | 6.90 |
| | | INV | 6.00 | 100 | 24.8 | 96.5 | 1.47 | 98.0 | 6.90 |
| 3 | 4 | UP | 6.00 | 100 | 23.5 | 91.4 | 1.46 | 97.3 | 6.88 |
| | | INV | 6.00 | 100 | 24.2 | 94.2 | 1.48 | 98.7 | 6.87 |
| 3 | 25 | UP | 6.00 | 100 | 21.7 | 84.4 | 1.43 | 95.3 | 6.88 |
| | | INV | 6.00 | 100 | 21.7 | 84.4 | 1.47 | 98.0 | 6.88 |

*UP — Upright
INV — Inverted

| Time (month) | Temp (°C.) | Position of Vial* | Particulate Matter No. of particles/vial | | | Description |
|---|---|---|---|---|---|---|
| | | | $\geq 10$ μm | $\geq 25$ μm | $\geq 50$ μm | |
| Intial | | | 23 | 2 | 0 | CCS* |
| 1 | 30 | UP | 109 | 61 | 16 | CCS |
| | | INV | 55 | 11 | 2 | CCS |
| 3 | 4 | UP | 29 | 2 | 0 | CCS |
| | | INV | 59 | 23 | 2 | CCS |
| 3 | 25 | UP | 141 | 76 | 17 | CCS |
| | | INV | 49 | 16 | 3 | CCS |

*CCS - Clear, colorless solution, essentially free of visible particles.

TABLE 4

Interferon Alfa-2b Stability Data on Example 5

| Time (month) | Temp (°C.) | Position of Vial* | Anti-Viral Assay (CPE) (×10⁶ IU/mL) | (% L.S.) | Protein Content (HPLC Assay) (mcg/mL) | (% of Initial) | m-Cresol Assay (mg/mL) | % LS | pH |
|---|---|---|---|---|---|---|---|---|---|
| Initial | | | 6.00 | 100 | 25.5 | 100 | 1.47 | 98.0 | 6.85 |
| 1 | 30 | UP | 6.00 | 100 | 19.5 | 76.5 | 1.49 | 99.3 | 6.82 |
| | | INV | 6.00 | 100 | 19.5 | 76.5 | 1.50 | 100 | 6.83 |
| 3 | 4 | UP | 6.00 | 100 | 24.0 | 94.1 | 1.43 | 95.3 | 6.81 |
| | | INV | 6.00 | 100 | 24.0 | 94.1 | 1.43 | 95.3 | 6.82 |
| 3 | 25 | UP | 6.00 | 100 | 20.2 | 79.2 | 1.39 | 92.7 | 6.82 |
| | | INV | 6.00 | 100 | 19.6 | 76.9 | 1.41 | 94.0 | 6.82 |

| Time (month) | Temp (°C.) | Position of Vial* | Particulate Matter No. of particles/vial ≧10μ | ≧25μ | ≧50μ | Description |
|---|---|---|---|---|---|---|
| Initial | | | 144 | 4 | 4 | CCS* |
| 1 | 30 | UP | 89 | 3 | 1 | CCS |
| | | INV | 64 | 1 | 0 | CCS |
| 3 | 4 | UP | 39 | 1 | 6 | CCS |
| | | INV | 77 | 19 | 6 | CCS |
| 3 | 25 | UP | 57 | 1 | 0 | CCS |
| | | INV | 140 | 24 | 1 | CCS |

*CCS - Clear, coloress solution, essentially free of visible particles.

Method of Manufacture for Examples 1 to 5

A. Compounding Paraben-Containing Aqueous Solution Formulations Such as Shown in Example 2

1. Charge approximately 80% of the water for injection at a temperature greater than 70° C. into a suitable jacketed compounding vessel equipped with an agitator.
2. Separately charge approximately 30% of the water for injection into another suitable vessel. Cool and maintain the water temperature between 20° and 25° C. Begin sparging and overlaying the water which will be used to bring the batch to final volume with filtered nitrogen to maintain a dissolved oxygen level at or below 0.25 ppm.
3. Charge and dissolve with mixing methylparaben and propylparaben into the compounding vessel in step 1 while maintaining the temperature of the solution between 70° and 80° C.
4. Cool the solution in step 3 to a temperature between 20° and 25° C. Sparge and overlay the solution with filtered nitrogen. Maintain a dissolved oxygen level at or below 0.25 ppm.
5. Charge and dissolve with mixing the following ingredients into the solution in step 4 while maintaining nitrogen sparging and overlaying:
   Sodium phosphate dibasic anhydrous
   Sodium phosphate monobasic monohydrate
   Edetate disodium
   Sodium chloride
6. Discontinue nitrogen sparging of the solution from step 5. Maintain nitrogen overlaying in the compounding vessel.
7. Charge and dissolve polysorbate 80 in approximately 50 mL of water for injection (for a 1-liter size batch) in a separate vessel. Transfer the polysorbate 80 solution into the solution from step 6.
8. Check the pH of the solution. It should be between 6.6 and 7.0. No pH adjustment is required.
9. Charge interferon alfa-2b bulk drug solution into the solution in step 8 while mixing.
10. Add water for injection that has been sparged with nitrogen (from step 2) to bring batch to final volume. Agitate solution gently until homogeneous.
11. Aseptically filter the solution through a sterilized filter that has been washed and tested for integrity. Collect the sterilized solution into a sterilized filling vessel that has been overlaid with sterile-filtered nitrogen. Integrity test the filter after filtration.
12. Overlay filling vessel in step 11 with sterile-filtered nitrogen and seal.

B. Compounding m-Cresol-Containing Aqueous Solution Formulations Such as Shown in Example 3

The manufacturing procedure used to prepare the aqueous solutions containing m-cresol as a preservative (such as shown in Example 3) is exactly the same as described hereinabove except the temperature of the solution in Step 3 is maintained between 20° and 25° C. and the m-cresol is charged after Step 6.

C. Compounding HSA-Free Aqueous Alfa Interferon Solution Formulations Under Ambient Air The manufacturing procedure used to prepare the HSA-free aqueous alfa interferon formulations of Examples 1 to 4 was used to prepare the formulations such as that of Example 5 except that all the steps were performed under ambient air; no nitrogen was sparged through the solution or overlaid upon it and ambient air (normally containing about 20% by volume of oxygen) occupied the headspace volume.

To maintain high chemical, physical and biological stability, it is preferred that the water used to prepare the aqueous alfa interferon solution as well as the so-formed aqueous alfa interferon solution be substantially free of dissolved oxygen, and the aqueous solution be made and stored with a headspace of an inert atmosphere, such as nitrogen, containing no more than about 4% volume of oxygen. By the term "substantially free of dissolved oxygen" as used herein is meant an oxygen level of no more than about 0.25 ppm at a water temperature of about 20°–25° C. Normally, this preferred dissolved oxygen level of 0.25 ppm is conveniently achieved by sparging an inert atmosphere, e.g. nitrogen gas into the water used to prepare the aqueous solutions (maintained at a temperature of about 20°–25° C.) for a time sufficient (e.g. about 30 minutes) to lower the dissolved oxygen to a value of no more than about 0.25 ppm. The sparging is continued throughout the manufacturing procedure to maintain the dissolved oxygen level at 0.25 ppm. We have found that aqueous formulations of the present invention which have a dissolved oxygen level of 1ppm and an oxygen content in the headspace of 7% by volume demonstrated significantly greater loss of chemical stability of the alfa interferon after 3 months of storage at 25° C. compared to a similar aqueous formulation having the preferred dissolved oxygen level of 0.25 ppm and an oxygen content in the headspace of 4% by volume stored under the same conditions.

A side-by-side comparison of the alfa-2b interferon solution stability data shown in Tables 3 and 4 shows that there is no significant stability difference between the aqueous solution formulations of the present invention which were prepared under the nitrogen/low oxygen conditions used in Example 4 and those prepared in accordance with Example 5 under ambient air during storage for 3 months at 4° C. In contrast, a comparison of the alfa-2b interferon stability in solutions of Examples 4 and 5 stored at higher temperatures, e.g. 25° and 30° C. shows the protective effect achieved by the preferred (safer) use of nitrogen sparging to effect low dissolved oxygen levels in the aqueous solution while simultaneously maintaining an oxygen content in the headspace at a value of no more than about 4% by volume.

The aqueous solution formulation of the present invention may be stored in any suitable washed and sterilized filing vessels or container such as 2-mL or 5-mL Type I flint glass vials stoppered with gray butyl rubber closures. The aqueous solution formulations of the present invention may also be stored in prefilled multi-dose syringes such as those useful for delivery of indictable solutions of drugs such as insulin. Typical suitable syringes include systems comprising a prefilled vial attached to a pen-type syringe such as the Novolet Novo Pen available from Novo Nordisk. Typical suitable systems include a prefilled, pen-type syringe which allows easy self-injection by the user as well as accurate, reproducible dose settings.

The aqueous solutions formulations of the present invention, such as present in the Examples may also be lyophilized to form a powder for reconstitution. The lyophilized alfa interferon powder is expected to maintain its chemical and biological stability when stored at 2° to 8° C. for at least 2 years.

We claim:

1. A process of preparing a stable, aqueous formulation of alfa interferon having at least 75% of alfa interferon biological activity and free of human blood-derived products comprising admixing $0.1 \times 10^6$ to $100 \times 10^6$ IU/mL alfa interferon with a buffer system capable of maintaining the pH within the range of 4.5 to 7.1, a chelating agent, a sorbitan mono-9-octadecenoate poly(oxy-1,2-ethanediyl) derivative, a tonicity agent, an antimicrobial preservative and sufficient water to make an aqueous solution wherein the dissolved oxygen level in said solution is maintained at a value of no more than about 0.25 ppm and a headspace of an inert atmosphere above said solution is simultaneously maintained at a value of less than about 4% oxygen by volume by sparging nitrogen into said water and said solution throughout the preparing of the stable, aqueous formulation.

2. An article of manufacture comprising a sterilized filling vessel and the formulation produced in accordance with the process of claim 1.

3. The article of manufacture of claim 2 wherein $10 \times 10^6$ IU/mL of interferon alfa-2b is used.

4. The article of claim 2 wherein interferon alfa-2b is used.

5. The article of manufacture of claim 2 wherein the sterilized filling vessel is a multidose glass vial.

6. The article of manufacture of claim 2 wherein the sterilized filling vessel is a prefilled syringe.

7. The article of manufacture of claim 6 wherein interferon alfa-2b is used.

8. The article of manufacture of claim 6 wherein $10 \times 10^6$ IU/mL of interferon alfa-2b is used.

9. The article of manufacture of claim 2 wherein the sterilized filling vessel is a single-dose vial.

10. The article of manufacture of claim 9 wherein interferon alfa-2b is used.

11. The article of manufacture of claim 9 wherein $10 \times 10^6$ IU/mL of interferon alfa-2b is used.

* * * * *